US007415980B2

(12) United States Patent
Hashiba

(10) Patent No.: US 7,415,980 B2
(45) Date of Patent: Aug. 26, 2008

(54) SUCTION DEVICE

(75) Inventor: Tomohiko Hashiba, 402 Minamiaoyama Manshon, 5-8, Minamiaoyama 2-chome, Minato-ku, Tokyo 107-0062 (JP)

(73) Assignees: Tomohiko Hashiba, Tokyo (JP); Bio Media Co., Ltd., Tokyo (JP)

( * ) Notice: Subject to any disclaimer, the term of this patent is extended or adjusted under 35 U.S.C. 154(b) by 729 days.

(21) Appl. No.: 10/488,059

(22) PCT Filed: Aug. 28, 2002

(86) PCT No.: PCT/JP02/08661

§ 371 (c)(1),
(2), (4) Date: Aug. 2, 2004

(87) PCT Pub. No.: WO03/020348

PCT Pub. Date: Mar. 13, 2003

(65) Prior Publication Data

US 2004/0244792 A1 Dec. 9, 2004

(30) Foreign Application Priority Data

Aug. 29, 2001 (JP) ............................ 2001-259161

(51) Int. Cl.
*A61M 11/00* (2006.01)

(52) U.S. Cl. ............................ 128/200.21; 128/200.14; 128/200.18; 128/203.12; 128/203.15; 261/78.1; 261/101

(58) Field of Classification Search ............ 128/200.14, 128/200.18, 203.12, 203.15, 200.21; 261/78.1, 261/79.1, 101, 102
See application file for complete search history.

(56) References Cited

U.S. PATENT DOCUMENTS

| | | | | |
|---|---|---|---|---|
| 5,775,320 | A * | 7/1998 | Patton et al. | 128/200.14 |
| 6,158,431 | A * | 12/2000 | Poole | 128/203.12 |
| 2001/0042927 | A1 * | 11/2001 | Rock | 261/79.1 |

FOREIGN PATENT DOCUMENTS

| | | |
|---|---|---|
| JP | 63-71048 | 4/1988 |
| JP | 04-141179 | 5/1992 |

(Continued)

*Primary Examiner*—Steven O Douglas
(74) *Attorney, Agent, or Firm*—Sterne, Kessler, Goldstein & Fox P.L.L.C.

(57) ABSTRACT

A suction device capable of spraying a liquid medicine or the like so that the particles have a set uniform diameter. It comprises a fine particle generating nozzle for generating fine particles of liquid medicine by pulverizing the liquid medicine by a gas, a separating vessel for separating the fine particles generated by the fine particle generating nozzle, a delivery section for delivering, only during suction, the superfine particles separated from the fine particles in the separating vessel, a particle size setting section for setting the particle size of the superfine particles delivered from the delivery section, a particle size detecting section for detecting the particle size of the superfine particles delivered from the delivery section, and a gas pressure control device for controlling the pressure of the gas fed to the fine particle generating nozzle so that the particle size of the superfine particles detected by the particle size detecting section may be equal to the particle size of the superfine particles set by the particle size setting section.

13 Claims, 8 Drawing Sheets

FOREIGN PATENT DOCUMENTS

| | | | | |
|---|---|---|---|---|
| JP | 7-501970 | | | 3/1995 |
| JP | 11-265780 | | | 9/1999 |
| JP | 2001-198218 | | | 7/2001 |
| JP | 2001198218 | A | * | 7/2001 |
| JP | 2001-233761 | | | 8/2001 |
| WO | WO 93/018911 | | | 2/1993 |

* cited by examiner

| No. | DIAMETER (μm) | | DIF (%) | VOLUME |
|---|---|---|---|---|
| 1 | 1.0 -> | 1.8 | 2.5 | |
| 2 | 1.8 -> | 2.7 | 98.1 | |
| 3 | 2.7 -> | 3.9 | 1.5 | |
| 4 | 3.9 -> | 5.0 | 0.0 | |
| 5 | 5.0 -> | 5.7 | 0.0 | |
| 6 | 5.7 -> | 6.4 | 0.0 | |
| 7 | 6.4 -> | 7.3 | 0.0 | |
| 8 | 7.3 -> | 8.2 | 0.0 | |
| 9 | 8.2 -> | 9.3 | 0.0 | |

SUCTION DEVICE

TECHNICAL FIELD

The present invention relates to a suction device for sucking superfine particles of a substance to be sprayed such as a medication and an agrichemical into a person, an animal, or the like.

BACKGROUND ART

Conventionally, a nebulizer for spraying a liquid medicine in the form of mist has been used for administering to respiratory disease. This nebulizer is directed for administering the liquid medicine in the form of mist to a patient using compressed air or supersonic vibration.

Further, even when inhalation toxicity testing of environmental pollutants, animal experiments performed in development of medications, and the like are performed, the environmental pollutants, the liquid medicine, and the like are administered to animals in the form of mist so that the tests are performed.

In the meanwhile, it is known that application sites are different depending on a particle size of the sprayed liquid medicine. FIG. 8 is a diagram for explaining a relationship between a particle size of the sprayed liquid medicine and an application site on a body. As shown in this drawing, the application sites to be contributed are different depending on the particle size of the sprayed liquid medicine; the throat when the particle size of the liquid medicine is 4.7 to 7 μm, the windpipe when the particle size is 3.3 to 4.7 μm, the bronchi when the particle size is 1.1 to 3.3 μm, and the like.

However, in the conventional nebulizer, the particle size of the liquid medicine to be sprayed has been roughly able to be changed depending on when the application site is the nose and when the application site is the throat, but the particle size of the liquid medicine to be sprayed has not been accurately able to be controlled. Further, since the particle size of the liquid medicine to be sprayed has a distribution having not uniform but constant particle size, the liquid medicine has been attached on other than the application site, and a large quantity of liquid medicine has been required to administer in order to obtain desired medical benefits.

Further, since the particle size of the sprayed environmental pollutants, the liquid medicine, and the like is not uniform also in the inhalation toxicity testing of the environmental pollutants, the animal experiments performed in development of the medications, and the like, errors along with the test results becomes large, and the accurate testing results are difficult to obtain.

Therefore, it is an object of the present invention to provide a suction device capable of spraying a liquid medicine and the like at a set uniform particle size.

DISCLOSURE OF THE INVENTION

A suction device according to a first aspect is characterized by comprising a fine particle generating nozzle for generating fine particles of a substance to be sprayed by pulverizing the substance to be sprayed made of liquid by a gas, a separating vessel for separating the fine particles generated by the fine particle generating nozzle, and a delivery section for delivering, only during suction, superfine particles separated from the fine particles in the separating vessel, a particle size setting means for setting a particle size of the superfine particles to be delivered from the delivery section, a particle size detecting means for detecting a particle size of the superfine particles to be delivered from the delivery section, and a first gas pressure control means for controlling a pressure of a gas to be fed to the fine particle generating nozzle such that the particle size of the superfine particles detected by the particle size detecting means is equal to the particle size of the superfine particles set by the particle size setting means.

According to the suction device of the first aspect, a substance to be sprayed can be sprayed as superfine particles having a uniform particle size set by the particle size setting means according to the application site, and the superfine particles of the substance to be sprayed can be sprayed only during suction from the delivery section. Therefore, the substance to be sprayed can be sprayed at the particle size according to the desired application site, and excessive substance to be sprayed can be prevented from spraying.

Further, a suction device according to a second aspect is characterized by comprising a fine particle generating nozzle for generating fine particles of a substance to be sprayed by pulverizing the substance to be sprayed made of liquid by a gas, a separating vessel for separating the fine particles generated by the fine particle generating nozzle, and a delivery section for delivering superfine particles separated from the fine particles in the separating vessel, a recovery processing section for recovering and processing the superfine particles which have not been sucked in the delivery section, a particle size setting means for setting a particle size of the superfine particles to be delivered from the delivery section, a particle size detecting means for detecting a particle size of the superfine particles to be delivered from the delivery section, and a first gas pressure control means for controlling a pressure of a gas to be fed to the fine particle generating nozzle such that the particle size of the superfine particles detected by the particle size detecting means is equal to the particle size of the superfine particles set by the particle size setting means.

According to the suction device of the second aspect, the substance to be sprayed is sprayed as superfine particles having a uniform particle size set by the particle size setting means according to the application site, and the superfine particles of the substance to be sprayed which have not been sucked are recovered and processed in the recovery processing section. Therefore, it is possible to prevent from affecting the environments even when the substance to be sprayed is toxic.

Further, a suction device according to a third aspect is characterized by further comprising a particle quantity setting means for setting the particle quantity of the superfine particles to be delivered from the delivery section, a particle quantity detecting means for detecting the particle quantity of the superfine particles to be delivered from the delivery section, and a substance-to-be-sprayed quantity control means for controlling the quantity of a substance to be sprayed to be supplied to the fine particle generating nozzle such that the particle quantity of the superfine particles detected by the particle quantity detecting means is equal to the particle quantity set by the particle quantity setting means.

According to the suction device of the third aspect, since the particle quantity of the superfine particles to be delivered from the delivery section is controlled to be the set quantity by the substance-to-be-sprayed quantity control means, the particle quantity of the substance to be sprayed can be accurately controlled according to his/her body type and symptom in the case of a person, and a size of an animal in the case of the animal.

Further, a suction device according to a fourth aspect is characterized by further comprising a secondary gas feeding means for feeding a secondary gas for increasing the fine particles in the separating vessel into the separating vessel, and a second gas pressure control means for controlling a pressure of a secondary gas to be fed by the secondary gas feeding means such that the particle size of the superfine particles detected by the particle size detecting means is equal to the particle size of the superfine particles set by the particle size setting means.

Further, a suction device according to a fifth aspect is characterized in that the separating vessel comprises a flow straightening member for guiding the fine particles generated by the fine particle generating nozzle to a lower part of the separating vessel, and fine particle sorting plates for restricting floating of the fine particles guided to the lower part of the separating vessel by the flow straightening member to perform sorting.

A suction device according to a sixth aspect is characterized in that the plurality of fine particle sorting plates respectively provided with a plurality of fine particle passing holes through which fine particles pass are disposed inside the separating vessel, and that a size of the fine particle passing holes provided at the fine particle sorting plate positioned at the lower side is larger than a size of the fine particle passing holes provided at the fine particle sorting plate positioned at the upper side.

Further, a suction device according to a seventh aspect is characterized by further comprising a charge supplying means for supplying charges to the superfine particles to be delivered from the delivery section, and a charge quantity control means for controlling the quantity of charges to be supplied to the superfine particles by the charge supplying means.

According to the suction device of the seventh aspect, since the charges can be supplied to the superfine particles to be delivered from the delivery section and the charge quantity can be controlled, the charge quantity is controlled so that the superfine particles can be securely attached to the application site.

BEST MODE FOR CARRYING OUT THE INVENTION

Figure 1:
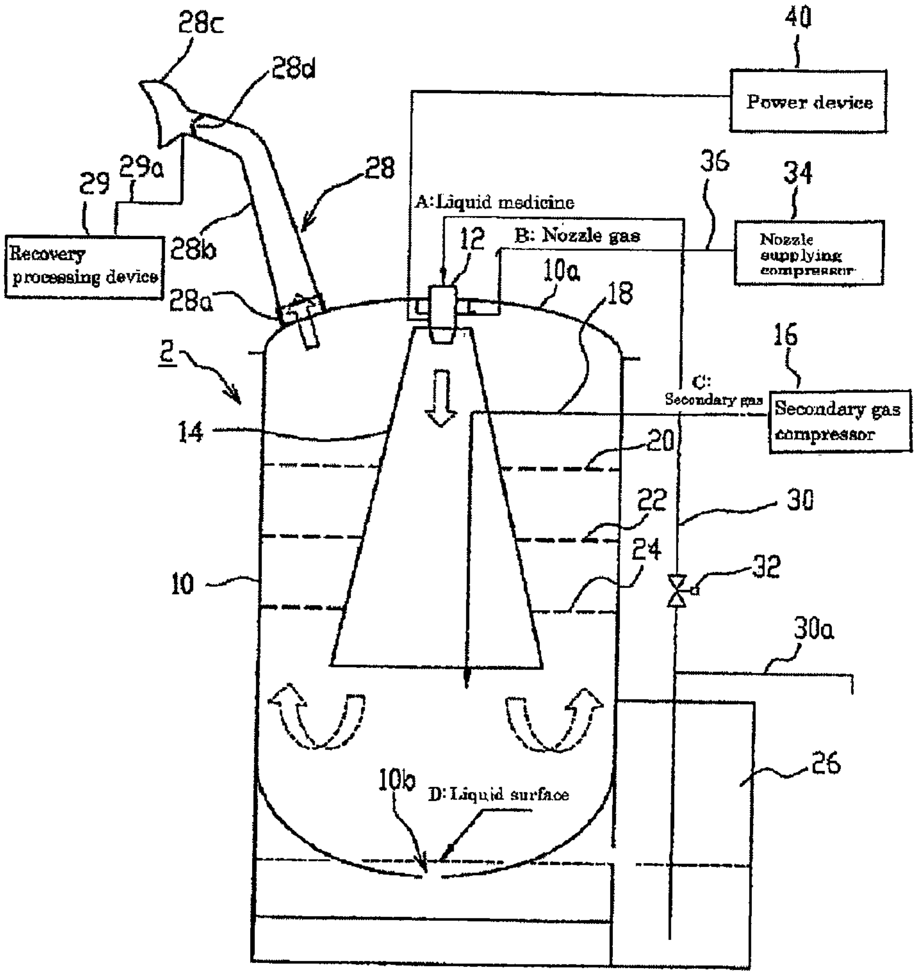
FIG. 1 is a schematic configuration diagram of a suction device according to an embodiment of the present invention.

Hereinafter, a suction device according to an embodiment of the present invention will be described. Here, reference numerals in the drawings are as follows. 2: suction device, 10: fine particle separating vessel, 12: two-fluid nozzle, 14: flow straightening cone, 16: secondary gas compressor, 20, 22, 24: fine particle sorting plate, 26: liquid medicine storing vessel, 28: delivery section, 28*c*: suction port, 28*d*: valve, 29: recovery processing device, 32: solenoid valve, 34: nozzle supplying compressor, 40: power device, 42: control device, 44*a*: particle size setting section, 44*b*: particle quantity setting section, 44*c*: electrostatic charge quantity setting section, S1: particle size detecting section, and S2: particle quantity detecting section.

Figure 2:
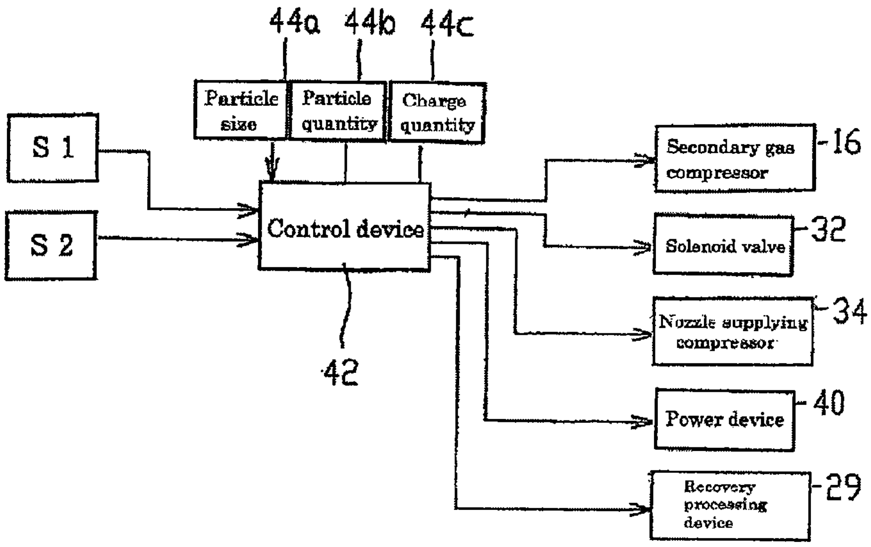
FIG. 2 is a system configuration diagram of the suction device according to the embodiment of the present invention.

FIG. 1 is a schematic configuration diagram of the suction device according to the embodiment of the present invention, and FIG. 2 is a system configuration diagram of the suction device.

This suction device 2 comprises a cylindrical fine particle separating vessel 10 whose lower end is closed and whose upper end is provided with a lid portion 10*a*. The lid portion 10*a* of this fine particle separating vessel 10 is provided with a two-fluid nozzle (fine particle generating nozzle) 12 for pulverizing a liquid medicine (substance to be sprayed) by a gas such as air. Here, the two-fluid nozzle 12 is directed for ejecting a gas from a gas ejection port toward an outer peripheral portion of the liquid medicine ejected from a liquid medicine ejection port provided at a tip end of the nozzle, and ejecting fine particles of the liquid medicine by pulverizing the liquid medicine by the gas.

There is provided inside the fine particle separating vessel 10 a flow straightening cone (flow straightening member) 14 for flow-straightening and guising the fine particles of the liquid medicine generated by the two-fluid nozzle 12 to a lower part of the fine particle separating vessel 10. Here, the tip end of the two-fluid nozzle 12 is disposed at an upper opening of the flow straightening cone 14. Further, a secondary gas feeding pipe 18 extending from a secondary gas compressor 16 is disposed inside the fine particle separating vessel 10, and a secondary gas such as air from the secondary gas compressor 16 is fed to the vicinity of a lower opening of the flow straightening cone 14. Further, there are provided inside the fine particle separating vessel 10 three fine particle sorting plates 20, 22, and 24 for controlling floating of the fine particles of the liquid medicine guided to the lower part of the fine particle separating vessel 10 by the flow straightening cone 14, and sorting the fine particles.

Figure 3:
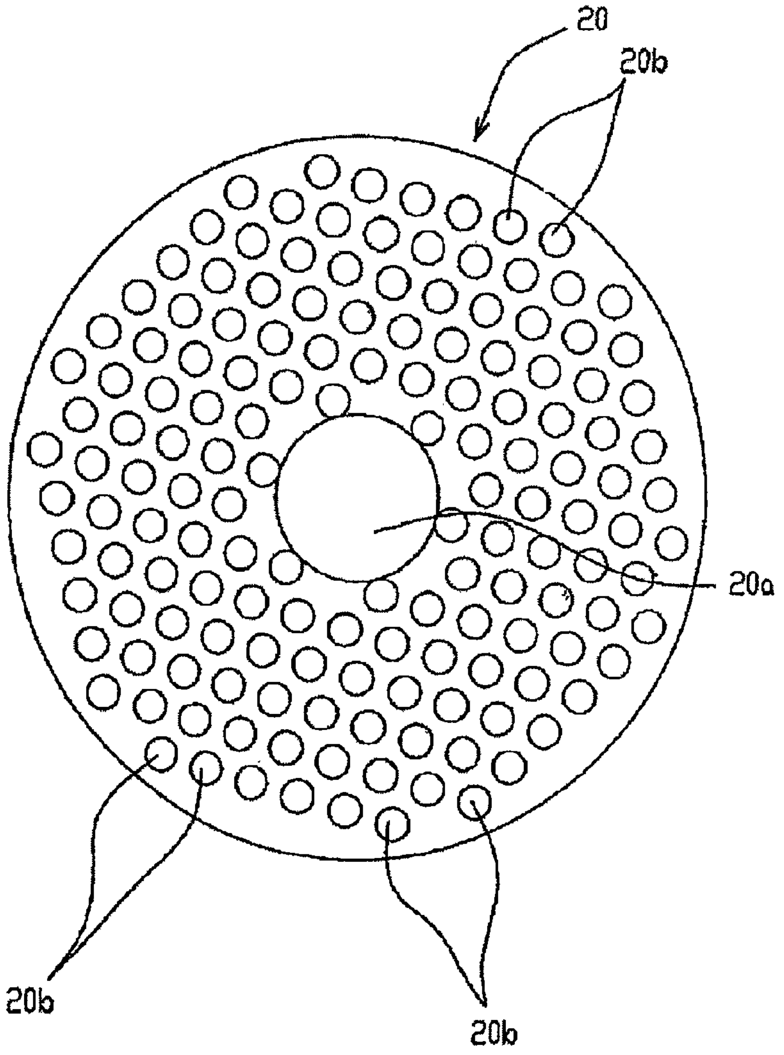
FIG. 3 is a diagram showing a fine particle sorting plate according to the embodiment of the present invention.
Figure 4:
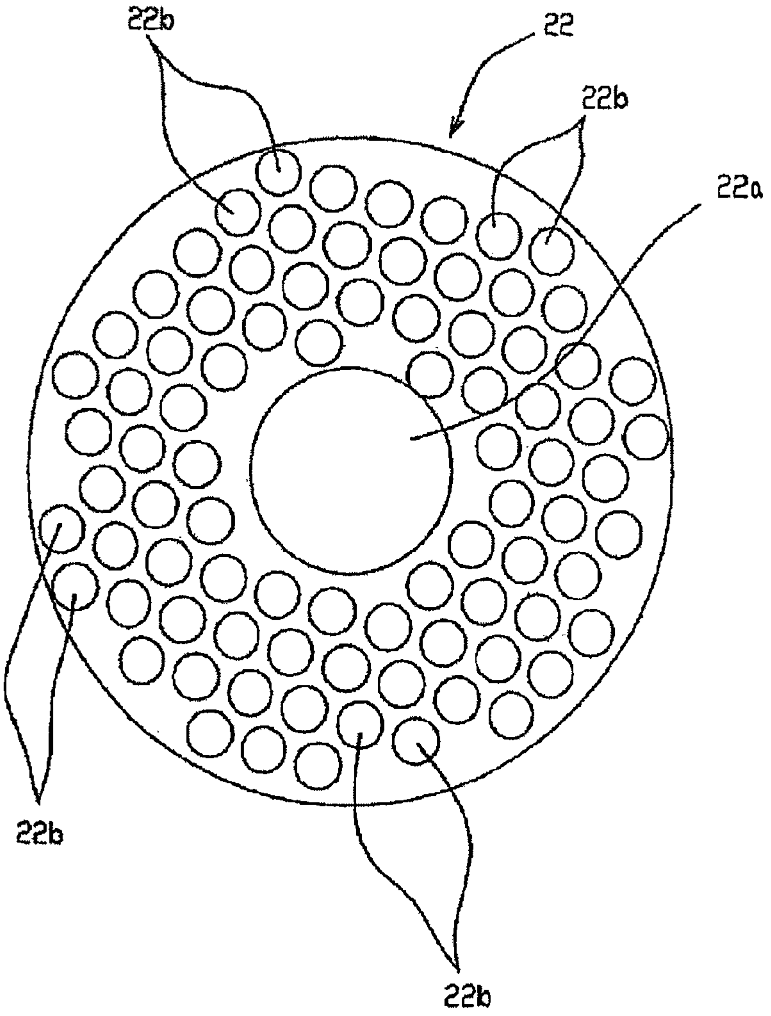
FIG. 4 is a diagram showing a fine particle sorting plate according to the embodiment of the present invention.
Figure 5:
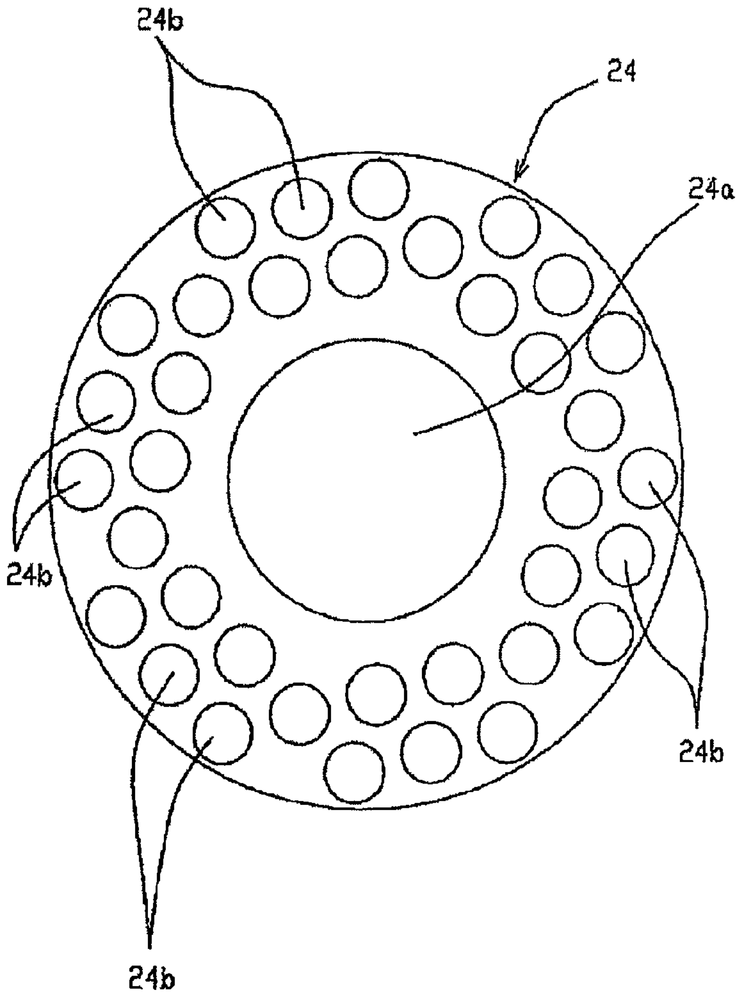
FIG. 5 is a diagram showing a fine particle sorting plate according to the embodiment of the present invention.

As shown in FIG. 3, the fine particle sorting plate 20 is a plate-shape member of a circular plate shape where an opening 20*a* through which the flow straightening cone 14 penetrates is provided at the center thereof, and is provided with a large number of fine particle passing holes 20*b*. Further, as shown in FIG. 4, the fine particle sorting plate 22 is a plate-shape member of a circular plate shape where an opening 22*a* through which the flow straightening cone 14 penetrates is provided at the center thereof, and is provided with a large number of fine particle passing holes 22*b*. The fine particle passing holes 22*b* are made to be larger than the fine particle passing holes 20*b* of the fine particle sorting plate 20. Furthermore, as shown in FIG. 5, the fine particle sorting plate 24 is a plate-shape member of a circular plate shape where an opening 24*a* through which the flow straightening cone 14 penetrates is provided at the center thereof, and is provided with a large number of fine particle passing holes 24*b*. The fine particle passing holes 24*b* are made to be larger than the fine particle passing holes 22*b* of the fine particle sorting plate 22.

A liquid medicine discharge port 10*b* communicated with a liquid medicine storing vessel 26 is provided at the bottom of the fine particle separating vessel 10. The liquid medicine retained at the bottom of the fine particle separating vessel 10 is discharged from the liquid medicine discharge port 10*b* and stored inside the liquid medicine storing vessel 26.

Further, a delivery section 28 for delivering the superfine particles separated from the fine particles inside the fine particle separating vessel 10 is provided at the lid portion 10*a* of the fine particle separating vessel 10. Here, the delivery section 28 is configured with a spray port attaching portion 28*a* attached at the lid portion 10*a* of the fine particle separating vessel 10, a spray guiding conduit 28*b* connected to the spray port attaching portion 28*a*, and a suction port 28*c* provided at a tip end of the spray guiding conduit 28*b*. There is provided a valve 28*d* for opening only during suction between the spray guiding conduit 28*b* and the suction port 28*c*. Further, the suction port 28*c* is provided with a recovery processing device 29 for recovering and processing the superfine particles of the liquid medicine via a superfine particle recovery pipe 29*a*.

Further, there is provided a liquid medicine supplying pipe 30 for supplying a liquid medicine to the two-fluid nozzle 12 between the liquid medicine storing vessel 26 and the two-fluid nozzle 12. This liquid medicine supplying pipe 30 is provided with a solenoid valve 32 for adjusting the quantity of the liquid medicine to be supplied to the two-fluid nozzle 12. The liquid medicine can be supplied to the two-fluid nozzle 12 via a branch supplying pipe 30*a* from other than the liquid medicine storing vessel 26. Further, there is provided a gas feeding pipe 36 for feeding a nozzle gas to the two-fluid nozzle 12 between the nozzle supplying compressor 34 and the two-fluid nozzle 12.

Further, a power device 40 for supplying charges to the superfine particles of the liquid medicine to be delivered from the suction port 28*c* of the delivery section 28 is connected to the two-fluid nozzle 12. A desired DC voltage is supplied to the two-fluid nozzle 12*c* by this power device 40 so that the superfine particles delivered from the suction port 28*c* are charged. The superfine particles are charged in this manner, thereby improving attachment efficiency of the liquid medicine to an application site.

A pressure of the secondary gas to be fed from the above secondary gas compressor 16 into the fine particle separating vessel 10, a pressure of the nozzle gas to be fed to the two-fluid nozzle 12 by the nozzle supplying compressor 34, and the quantity of the liquid medicine to be supplied to the two-fluid nozzle 12 via the solenoid valve 32 are controlled by a control device 42 (refer to FIG. 2). Further, the quantity of charges (the quantity of electrostatic charges) to be supplied to the two-fluid nozzle 12 by the power device 40 is controlled by the control device 42. In other words, the control device 42 functions as a first gas pressure control means for controlling a pressure of the nozzle gas to be fed to the two-fluid nozzle 12, a second gas pressure control means for controlling a pressure of the secondary gas to be fed into the fine particle separating vessel 10, a liquid medicine quantity control means for controlling the quantity of the liquid medicine to be supplied to the two-fluid nozzle 12, and a charge quantity control means for controlling the quantity of charges to be supplied to the suction port 28*c* of the delivery section 28.

Further, a particle size detecting section S1 for detecting a distribution of particle sizes of the superfine particles to be delivered from the suction port 28*c* of the delivery section 28, and a particle quantity detecting section S2 for detecting the particle quantity of the superfine particles are connected to the control device 42, and detection values from the particle size detecting section S1 and the particle quantity detecting section S2 are input therein. Further, to the control device 42 are connected a particle size setting section 44*a* for setting a particle size of the superfine particles to be delivered from the suction port 28*c* of the delivery section 28, a particle quantity setting section 44*b* for setting the particle quantity of the superfine particles, and an electrostatic charge quantity setting section 44*c* for setting the quantity of electrostatic charges (quantity of charges to be supplied) of the superfine particles.

Next, generation of the superfine particles by this suction device 2 will be described. In the following description, a description will be given by way of an example where the liquid medicine is supplied to the two-fluid nozzle 12 and air as a nozzle gas and a secondary gas is supplied so that the superfine particles of the liquid medicine are generated to be sucked by a person.

At first, a particle size of the superfine particles of the liquid medicine to be delivered from the suction port 28*c* of the delivery section 28 is set by the particle size setting section 44*a*, and the particle quantity of the superfine particles of the liquid medicine to be delivered from the suction port 28*c* of the delivery section 28 is set by the particle quantity setting section 44*b*. In other words, an appropriate particle size is set according to a site to be medicated, and the particle quantity is set according to a body type, a symptom, and the like of a person to be medicated.

After the setting of the particle size of the superfine particles and the setting of the particle quantity of the superfine particles are terminated, the superfine particles of the liquid medicine are generated. In other words, in this suction device 2, when air (nozzle gas) is fed from the nozzle supplying compressor 34 to the two-fluid nozzle 12 via the gas feeding pipe 36, this air is ejected from the gas ejection port at the tip end of the two-fluid nozzle 12, and the liquid medicine inside the liquid medicine storing vessel 26 is sucked up by this ejection force to be supplied to the two-fluid nozzle 12 via the liquid medicine supplying pipe 30.

In the two-fluid nozzle 12, the liquid medicine to be ejected from the liquid medicine ejection port is pulverized by the air ejected from the gas ejection port so that the fine particles of the liquid medicine are ejected. The fine particles of the liquid medicine ejected from this two-fluid nozzle 12 are guided through the flow straightening cone 14 to the lower part of the fine particle separating vessel 10. On the other hand, the air (secondary gas) from the secondary gas compressor 16 is fed to the vicinity of the lower opening of the flow straightening cone 14 via the secondary gas feeding pipe 18.

While the fine particles of the liquid medicine guided to the lower part of the fine particle separating vessel 10 are restricted from floating due to an upward flow of the air (nozzle air) and the secondary air fed from the two-fluid nozzle 12 by the fine particle sorting plates 20, 22, and 24, they gradually float inside the fine particle separating vessel 10 through the fine particle passing holes 20*b*, 22*b*, and 24*b* provided at the fine particle sorting plates 20, 22, and 24, respectively. In other words, the fine particles of the liquid medicine passed through the fine particle sorting plate 24 are first restricted from floating by the fine particle sorting plate 22, and the fine particles of the liquid medicine having a predetermined particle size are retained between the fine particle sorting plate 24 and the fine particle sorting plate 22. Here, the fine particles of the liquid medicine having a large particle size drop on the bottom of the fine particle separating vessel 10 due to the force of gravity.

Further, the fine particles of the liquid medicine passed through the fine particle sorting plate 22 are restricted from floating by the fine particle sorting plate 20, and the fine particles of the liquid medicine having a predetermined particle size are retained between the fine particle sorting plate 22 and the fine particle sorting plate 20. Here, the fine particles of the liquid medicine having a large particle size drop on the bottom of the fine particle separating vessel 10 due to the force of gravity. The particle size of the fine particles of the liquid medicine retained between the fine particle sorting plate 22 and the fine particle sorting plate 20 is made smaller than the particle size of the fine particles of the liquid medicine retained between the fine particle sorting plate 24 and the fine particle sorting plate 22.

As the fine particles of the liquid medicine float inside the fine particle separating vessel 10 in this manner, the fine particles of the liquid medicine having a large particle size drop on the bottom of the fine particle separating vessel 10, and only the superfine particles of the liquid medicine having a uniform particle size are delivered from the delivery section 28 of the fine particle separating vessel 10. The liquid medicine retained at the bottom of the fine particle separating vessel 10 is discharged from the liquid medicine discharge port 10*b*, and stored in the liquid medicine storing vessel 26 to be reused.

A distribution of the particle size of the superfine particles of the liquid medicine delivered from the suction port 28*c* of the delivery section 28 is detected by the particle size detecting section S1, and the particle quantity of the superfine particles of the liquid medicine is detected by the particle quantity detecting section S2. The detection values detected by the particle size detecting section S1 and the particle quantity detecting section S2 are input into the control device 42. In the control device 42, control signals are output to the secondary gas compressor 16, the solenoid valve 32, and the nozzle supplying compressor 34, the pressure of the air (nozzle gas) to be fed to the two-fluid nozzle 12 and the quantity of the liquid medicine to be supplied to the two-fluid nozzle 12 are controlled, and the pressure of the secondary gas to be fed to the fine particle separating vessel 10 is controlled such that the particle size of the superfine particles of the liquid medicine to be delivered from the suction port 28*c* of the delivery section 28 is equal to a value set by the particle size setting section 44*a*, and the particle quantity of the superfine particles of the liquid medicine is equal to a value set by the particle quantity setting section 44*b*.

In other words, in the control device 42, when the particle size of the superfine particles of the liquid medicine detected by the particle size detecting section S1 is larger than that set by the particle size setting section 44*a*, the nozzle supplying compressor 34 is controlled so that the pressure of the air (nozzle gas) to be fed to the two-fluid nozzle 12 is increased. Further, the secondary gas compressor 16 is controlled to increase the pressure of the air (secondary gas) to be fed into the fine particle separating vessel 10. Thereby, the particle size of the superfine particles of the liquid medicine to be delivered from the suction port 28*c* is made smaller.

On the other hand, when the particle size of the superfine particles of the liquid medicine detected by the particle size detecting section S1 is smaller than that set by the particle size setting section 44*a*, the nozzle supplying compressor 34 is controlled to reduce the pressure of the air (nozzle gas) to be fed to the two-fluid nozzle 12. Further, the secondary gas compressor 16 is controlled to reduce the pressure of the air (secondary gas) to be fed into the fine particle separating vessel 10. Thereby, the particle size of the superfine particles to be delivered from the suction port 28*c* is made smaller.

Although either the pressure of the air (nozzle gas) to be fed to the two-fluid nozzle 12 or the pressure of the air (secondary gas) to be fed into the fine particle separating vessel 10 is controlled so that the particle size of the superfine particles of the liquid medicine to be delivered from the suction port 28*c* can be controlled, both the pressure of the air (nozzle gas) to be fed to the two-fluid nozzle 12 and the pressure of the air (secondary gas) to be fed into the fine particle separating vessel 10 are controlled so that the particle size of the superfine particles of the liquid medicine can be controlled more accurately.

Further, when the quantity of the fine particles of the liquid medicine detected by the particle quantity detecting section S2 is smaller than the quantity set by the particle quantity setting section 44*b*, a control signal is output to the solenoid valve 32 to increase the quantity of the liquid medicine to be supplied to the two-fluid nozzle 12. Thereby, the particle quantity of the superfine particles of the liquid medicine to be delivered from the suction port 28*c* is increased. On the other hand, when the quantity of the fine particles of the liquid medicine detected by the particle quantity detecting section S2 is larger than the quantity set by the particle quantity setting section 44*b*, a control signal is output to the solenoid valve 32 to reduce the quantity of the liquid medicine to be supplied to the two-fluid nozzle 12. Thereby, the particle quantity of the superfine particles of the liquid medicine to be delivered from the suction port 28*c* is made smaller.

In this suction device 2, the above control is repeated until the particle size of the superfine particles of the liquid medicine detected by the particle size detecting section S1 is equal to the particle size set by the particle size setting section 44*a* and the particle quantity of the liquid medicine detected by the particle quantity detecting section S2 is equal to the particle quantity set by the particle quantity setting section 44*b*, and then suction is started.

In this suction device 2, the valve 28 is opened only during suction so that the superfine particles of the liquid medicine can be delivered/sucked with respect to the suction port 28*c*. Further, the superfine particles of the liquid medicine which have been delivered to the suction port 28*c* and have not been sucked therefrom are recovered and processed in the recovery processing device 29.

According to the superfine particle generating device 2 of this embodiment, the liquid medicine can be sprayed as the superfine particles having a uniform particle size set by the particle size setting means, and the superfine particles of the liquid medicine can be delivered only during suction. Therefore, since the superfine particles of the liquid medicine can be sprayed at the particle size according to a desired application site, large medical benefits can be obtained by a small quantity of liquid medicine. Further, since it is possible to prevent excessive liquid medicine from spraying, the consumption of the liquid medicine can be reduced.

Further, the liquid medicine is sprayed as the superfine particles having a uniform particle size set by the particle size setting means, and the superfine particles of the liquid medicine which have not been sucked is recovered and processed in the recovery processing section. Therefore, it is possible to prevent from affecting the environments even when the liquid medicine is toxic.

Further, since the particle quantity of the superfine particles to be delivered from the suction port 28*c* is controlled to be the set quantity, the particle quantity of the liquid medicine can be accurately controlled according to a body type and a symptom of the person.

In the suction device 2 according to the above embodiment, the superfine particles of the liquid medicine to be delivered from the suction port 28*c* of the delivery section 28 can be charged by the electrostatic charge quantity setting section 44*c*. In other words, when the electrostatic charge quantity is set by the electrostatic charge quantity setting section 44*c*, the control device 42 outputs a control signal to the power device 40 on the basis of the set value, and the quantity of charges to be supplied to the two-fluid nozzle 12 is controlled by the power device 40. Therefore, the charge quantity is controlled so that the superfine particles can be securely attached on the application site.

Further, although a description has been given by way of an example where the superfine particles of the liquid medicine are generated to be sucked by a person in the above embodiment, liquid medicines, environmental pollutants, and the like are treated as substances to be sprayed, and the superfine particles of the substances to be sprayed are sucked into animals so that animal experiments can be performed. In this case, since the set uniform superfine particles can be used for the experiments, accurate experiment results can be obtained.

Further, in the above embodiment, although when air is fed to the two-fluid nozzle 12, this air is ejected from the gas ejection port at the tip end of the two-fluid nozzle 12 and the liquid medicine inside the liquid medicine storing vessel 26 is sucked up by this ejection force to be supplied to the two-fluid nozzle 12, in the case where the viscosity of the liquid medicine is remarkably high, the liquid medicine in the two-fluid nozzle 12 is guided to the liquid medicine ejection port using a pump or the like so that the superfine particles of the liquid medicine can be similarly generated.

Further, since this suction device can generate superfine particles of the substance to be sprayed having a uniform particle size, even when it is used for suction tests and the like performed in safety tests of medications, agrichemicals, and the like, toxicity tests of various chemical substances in working environments, researches on air pollutants and environmental hormones, and the like, accurate test results can be obtained.

Figure 6:
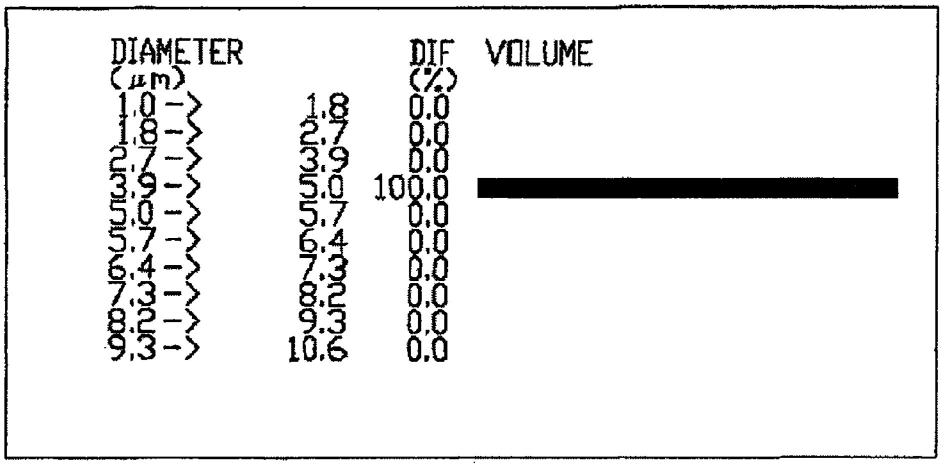
FIG. 6 is a diagram showing a measurement result of a particle size of superfine particles generated by the suction device and an existence ratio per particle size according to the embodiment of the present invention.

Next, the measurement results of a particle size of the superfine particles of the liquid medicine generated in this suction device 2 and an existence ratio per particle size are shown. FIG. 6 is a diagram showing the results where the particle size of the superfine particles is set at 4 μm by the particle size setting section 44*a*, that is, the particle size is set such that the application site is the windpipe, and the superfine particles of the liquid medicine are generated in a state where the predetermined particle quantity according to a body type and the like of a patient is set by the particle quantity setting section 44*b* so that the particle size of the superfine particles and the particle quantity of the superfine particles (existence ratio per particle size) are measured. As shown in this drawing, it is confirmed that the superfine particles of the liquid medicine having the particle size and the particle quantity set according to the application site of the liquid medicine, the body type of the patient, and the like can be generated.

Figure 7:
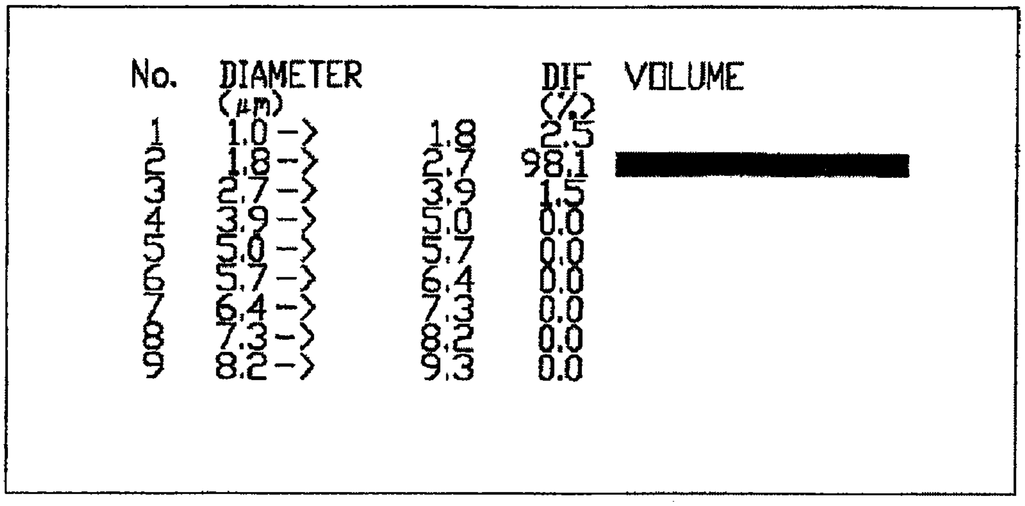
FIG. 7 is a diagram showing a measurement result of a particle size of superfine particles generated by the suction device and an existence ratio per particle size according to the embodiment of the present invention.
Figure 8:
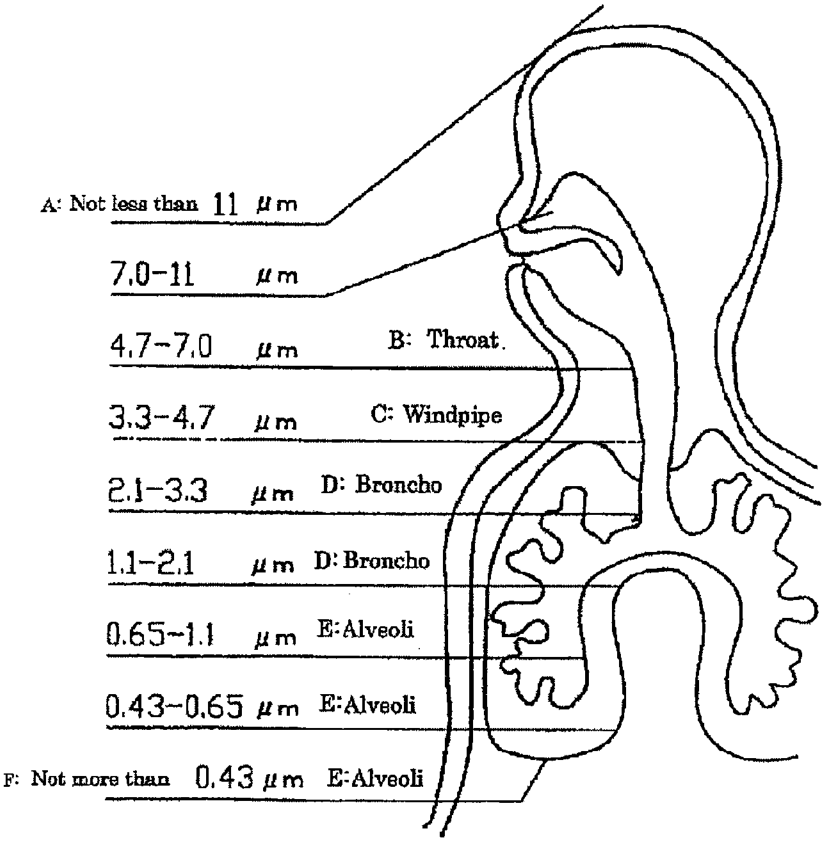
FIG. 8 is a diagram showing a relationship between a particle size of a liquid medicine and an application site.

Further, FIG. 7 is a diagram showing results where the particle size of the superfine particles is set at 2 μm by the particle size setting section 44*a*, that is, the particle size is set such that the application site is the bronchi, and the superfine particles of the liquid medicine are generated in a state where the predetermined particle quantity according to a body type and the like of a patient is set by the particle quantity setting section 44*b* so that the particle size of the superfine particles and the particle quantity of the superfine particles (existence ration per particle size) are measured. As shown in this drawing, it is confirmed that the superfine particles having the particle size and the particle quantity set according to the application site of the liquid medicine, the body type of the patient, and the like can be generated.

INDUSTRIAL APPLICABILITY

According to the present invention, the substance to be sprayed can be sprayed as the superfine particles having a uniform particle size set according to the application site by the particle size setting means, and the superfine particles of the substance to be sprayed can be delivered from the delivery section only during suction. Therefore, the substance to be sprayed can be sprayed at the particle size according to a desired application site, and excessive substance to be sprayed can be prevented from spraying.

Further, the substance to be sprayed is sprayed as the superfine particles having a uniform particle size set according to the application site by the particle size setting means, and the superfine particles of the substance to be sprayed which have not been sucked are recovered and processed in the recovery processing section. Therefore, even when the substance to be sprayed is toxic, it is possible to prevent from affecting the environments.

Further, since the particle quantity of the superfine particles to be delivered from the delivery section is controlled to be the set quantity by the substance-to-be-sprayed quantity control means, the particle quantity of the substance to be sprayed can be accurately controlled according to a body type and a symptom of a person when the person sucks, and according to a size of an animal in the case of an animal experiment.

Furthermore, since the charges can be supplied to the superfine particles to be delivered from the delivery section and the charge quantity can be controlled, the charge quantity is controlled so that the superfine particles can be securely attached to the application site.

The invention claimed is:

1. A suction device comprising:

a fine particle generating nozzle for generating fine particles of a substance to be sprayed by pulverizing the substance to be sprayed made of liquid by a gas;

a separating vessel for separating the fine particles generated by the fine particle generating nozzle;

a delivery section for delivering, only during suction, superfine particles separated from the fine particles in the separating vessel;

a particle size setting means for setting a particle size of the superfine particles to be delivered from the delivery section;

a particle size detecting means for detecting a particle size of the superfine particles to be delivered from the delivery section;

a first gas pressure control means for controlling a pressure of a gas to be fed to the fine particle generating nozzle such that the particle size of the superfine particles detected by the particle size detecting means is equal to the particle size of the superfine particles set by the particle size setting means;

a secondary gas feeding means for feeding a secondary gas for increasing the fine particles in the separating vessel into the separating vessel; and a second gas pressure control means for controlling a pressure of the secondary gas to be fed by the secondary gas feeding means such that the particle size of the superfine particles detected by the particle size detecting means is equal to the particle size of the superfine particles set by the particle size setting means.

2. A suction device comprising:

a fine particle generating nozzle for generating fine particles of a substance to be sprayed by pulverizing the substance to be sprayed made of liquid by a gas;

a separating vessel for separating the fine particles generated by the fine particle generating nozzle;

a delivery section for delivering, only during suction, superfine particles separated from the fine particles in the separating vessel;

a recovery processing section for recovering and processing the superfine particles which have not been sucked in the delivery section;

a particle size setting means for setting a particle size of the superfine particles to be delivered from the delivery section;

a particle size detecting means for detecting a particle size of the superfine particles to be delivered from the delivery section;

a first gas pressure control means for controlling a pressure of a gas to be fed to the fine particle generating nozzle such that the particle size of the superfine particles detected by the particle size detecting means is equal to the particle size of the superfine particles set by the particle size setting means;

a secondary gas feeding means for feeding a secondary gas for increasing the fine particles in the separating vessel into the separating vessel; and a second gas pressure control means for controlling a pressure of the secondary gas to be fed by the secondary gas feeding means such that the particle size of the superfine particles detected by the particle size detecting means is equal to the particle size of the superfine particles set by the particle size setting means.

3. A suction device comprising:

a fine particle generating nozzle for generating fine particles of a substance to be sprayed by pulverizing the substance to be sprayed made of liquid by a gas;

a separating vessel for separating the fine particles generated by the fine particle generating nozzle;

a delivery section for delivering, only during suction, superfine particles separated from the fine particles in the separating vessel;

a particle size setting means for setting a particle size of the superfine particles to be delivered from the delivery section;

a particle size detecting means for detecting a particle size of the superfine particles to be delivered from the delivery section;

a first gas pressure control means for controlling a pressure of a gas to be fed to the fine particle generating nozzle such that the particle size of the superfine particles detected by the particle size detecting means is equal to the particle size of the superfine particles set by the particle size setting means;

a secondary gas feeding means for feeding a secondary gas for increasing the fine particles in the separating vessel into the separating vessel; and a second gas pressure control means for controlling a pressure of the secondary gas to be fed by the secondary gas feeding means such that the particle size of the superfine particles detected by the particle size detecting means is equal to the particle size of the superfine particles set by the particle size setting means, wherein the separating vessel comprises a flow straightening member for guiding the fine particles generated by the fine particle generating nozzle to a lower part of the separating vessel, and fine particle sorting plates for restricting floating of the fine particles guided to the lower part of the separating vessel by the flow straightening member to perform sorting.

4. A suction device comprising:

a fine particle generating nozzle for generating fine particles of a substance to be sprayed by pulverizing the substance to be sprayed made of liquid by a gas;

a separating vessel for separating the fine particles generated by the fine particle generating nozzle;

a delivery section for delivering, only during suction, superfine particles separated from the fine particles in the separating vessel;

a recovery processing section for recovering and processing the superfine particles which have not been sucked in the delivery section;

a particle size setting means for setting a particle size of the superfine particles to be delivered from the delivery section;

a particle size detecting means for detecting a particle size of the superfine particles to be delivered from the delivery section;

a first gas pressure control means for controlling a pressure of a gas to be fed to the fine particle generating nozzle such that the particle size of the superfine particles detected by the particle size detecting means is equal to the particle size of the superfine particles set by the particle size setting means;

a secondary gas feeding means for feeding a secondary gas for increasing the fine particles in the separating vessel into the separating vessel; and a second gas pressure control means for controlling a pressure of the secondary gas to be fed by the secondary gas feeding means such that the particle size of the superfine particles detected by the particle size detecting means is equal to the particle size of the superfine particles set by the particle size setting means, wherein the separating vessel comprises a flow straightening member for guiding the fine particles generated by the fine particle generating nozzle to a lower part of the separating vessel, and fine particle sorting plates for restricting floating of the fine particles guided to the lower part of the separating vessel by the flow straightening member to perform sorting.

5. A suction device comprising:

a fine particle generating nozzle for generating fine particles of a substance to be sprayed by pulverizing the substance to be sprayed made of liquid by a gas;

a separating vessel for separating the fine particles generated by the fine particle generating nozzle;

a delivery section for delivering, only during suction, superfine particles separated from the fine particles in the separating vessel;

a particle size setting means for setting a particle size of the superfine particles to be delivered from the delivery section;

a particle size detecting means for detecting a particle size of the superfine particles to be delivered from the delivery section;

a first gas pressure control means for controlling a pressure of a gas to be fed to the fine particle generating nozzle such that the particle size of the superfine particles detected by the particle size detecting means is equal to the particle size of the superfine particles set by the particle size setting means;

a secondary gas feeding means for feeding a secondary gas for increasing the fine particles in the separating vessel into the separating vessel; and a second gas pressure control means for controlling a pressure of the secondary gas to be fed by the secondary gas feeding means such that the particle size of the superfine particles detected by the particle size detecting means is equal to the particle size of the superfine particles set by the particle size setting means, wherein the separating vessel comprises a flow straightening member for guiding the fine particles generated by the fine particle generating nozzle to a lower part of the separating vessel, and fine particle sorting plates for restricting floating of the fine particles guided to the lower part of the separating vessel by the flow straightening member to perform sorting, wherein the plurality of fine particle sorting plates respectively provided with a plurality of fine particle passing holes through which fine particles pass are disposed inside the separating vessel, and a size of the fine particle passing holes provided at the fine particle sorting plate positioned at a lower side of the separating vessel is larger than a size of the fine particle passing holes provided at the fine particle sorting plate positioned at an upper side of the separating vessel.

6. A suction device comprising:

a fine particle generating nozzle for generating fine particles of a substance to be sprayed by pulverizing the substance to be sprayed made of liquid by a gas;

a separating vessel for separating the fine particles generated by the fine particle generating nozzle;

a delivery section for delivering, only during suction, superfine particles separated from the fine particles in the separating vessel;

a recovery processing section for recovering and processing the superfine particles which have not been sucked in the delivery section;

a particle size setting means for setting a particle size of the superfine particles to be delivered from the delivery section;

a particle size detecting means for detecting a particle size of the superfine particles to be delivered from the delivery section;

a first gas pressure control means for controlling a pressure of a gas to be fed to the fine particle generating nozzle such that the particle size of the superfine particles detected by the particle size detecting means is equal to the particle size of the superfine particles set by the particle size setting means;

a secondary gas feeding means for feeding a secondary gas for increasing the fine particles in the separating vessel into the separating vessel; and a second gas pressure control means for controlling a pressure of the secondary gas to be fed by the secondary gas feeding means such that the particle size of the superfine particles detected by the particle size detecting means is equal to the particle size of the superfine particles set by the particle size setting means, wherein the separating vessel comprises a flow straightening member for guiding the fine particles generated by the fine particle generating nozzle to a lower part of the separating vessel, and fine particle sorting plates for restricting floating of the fine particles guided to the lower part of the separating vessel by the flow straightening member to perform sorting, wherein the plurality of fine particle sorting plates respectively provided with a plurality of fine particle passing holes through which fine particles pass are disposed inside the separating vessel, and a size of the fine particle passing holes provided at the fine particle sorting plate positioned at a lower side of the separating vessel is larger than a size of the fine particle passing holes provided at the fine particle sorting plate positioned at an upper side of the separating vessel.

7. A suction device comprising:

a fine particle generating nozzle for generating fine particles of a substance to be sprayed by pulverizing the substance to be sprayed made of liquid by a gas;

a separating vessel for separating the fine particles generated by the fine particle generating nozzle;

a delivery section for delivering, only during suction, superfine particles separated from the fine particles in the separating vessel;

a particle size setting means for setting a particle size of the superfine particles to be delivered from the delivery section;

a particle size detecting means for detecting a particle size of the superfine particles to be delivered from the delivery section;

a first gas pressure control means for controlling a pressure of a gas to be fed to the fine particle generating nozzle such that the particle size of the superfine particles detected by the particle size detecting means is equal to the particle size of the superfine particles set by the particle size setting means;

a secondary gas feeding means for feeding a secondary gas for increasing the fine particles in the separating vessel into the separating vessel;

a second gas pressure control means for controlling a pressure of the secondary gas to be fed by the secondary gas feeding means such that the particle size of the superfine particles detected by the particle size detecting means is equal to the particle size of the superfine particles set by the particle size setting means;

a charge supplying means for supplying charges to the superfine particles to be delivered from the delivery section; and a charge quantity control means for controlling the quantity of charges to be supplied to the superfine particles by the charge supplying means.

8. A suction device comprising:

a fine particle generating nozzle for generating fine particles of a substance to be sprayed by pulverizing the substance to be sprayed made of liquid by a gas;

a separating vessel for separating the fine particles generated by the fine particle generating nozzle;

a delivery section for delivering, only during suction, superfine particles separated from the fine particles in the separating vessel;

a recovery processing section for recovering and processing the superfine particles which have not been sucked in the delivery section;

a particle size setting means for setting a particle size of the superfine particles to be delivered from the delivery section;

a particle size detecting means for detecting a particle size of the superfine particles to be delivered from the delivery section;

a first gas pressure control means for controlling a pressure of a gas to be fed to the fine particle generating nozzle such that the particle size of the superfine particles detected by the particle size detecting means is equal to the particle size of the superfine particles set by the particle size setting means;

a secondary gas feeding means for feeding a secondary gas for increasing the fine particles in the separating vessel into the separating vessel;

a second gas pressure control means for controlling a pressure of the secondary gas to be fed by the secondary gas feeding means such that the particle size of the superfine particles detected by the particle size detecting means is equal to the particle size of the superfine particles set by the particle size setting means;

a charge supplying means for supplying charges to the superfine particles to be delivered from the delivery section; and a charge quantity control means for controlling the quantity of charges to be supplied to the superfine particles by the charge supplying means.

9. A suction device comprising:

a fine particle generating nozzle for generating fine particles of a substance to be sprayed by pulverizing the substance to be sprayed made of liquid by a gas;

a separating vessel for separating the fine particles generated by the fine particle generating nozzle;

a delivery section for delivering, only during suction, superfine particles separated from the fine particles in the separating vessel;

a particle size setting means for setting a particle size of the superfine particles to be delivered from the delivery section;

a particle size detecting means for detecting a particle size of the superfine particles to be delivered from the delivery section;

a first gas pressure control means for controlling a pressure of a gas to be fed to the fine particle generating nozzle such that the particle size of the superfine particles detected by the particle size detecting means is equal to the particle size of the superfine particles set by the particle size setting means;

a secondary gas feeding means for feeding a secondary gas for increasing the fine particles in the separating vessel into the separating vessel;

a second gas pressure control means for controlling a pressure of the secondary gas to be fed by the secondary gas feeding means such that the particle size of the superfine particles detected by the particle size detecting means is equal to the particle size of the superfine particles set by the particle size setting means;

a charge supplying means for supplying charges to the superfine particles to be delivered from the delivery section; and a charge quantity control means for controlling the quantity of charges to be supplied to the superfine particles by the charge supplying means, wherein the separating vessel comprises a flow straightening member for guiding the fine particles generated by the fine particle generating nozzle to a lower part of the separating vessel, and fine particle sorting plates for restricting floating of the fine particles guided to the lower part of the separating vessel by the flow straightening member to perform sorting.

10. A suction device comprising:

a fine particle generating nozzle for generating fine particles of a substance to be sprayed by pulverizing the substance to be sprayed made of liquid by a gas;

a separating vessel for separating the fine particles generated by the fine particle generating nozzle;

a delivery section for delivering, only during suction, superfine particles separated from the fine particles in the separating vessel;

a recovery processing section for recovering and processing the superfine particles which have not been sucked in the delivery section;

a particle size setting means for setting a particle size of the superfine particles to be delivered from the delivery section;

a particle size detecting means for detecting a particle size of the superfine particles to be delivered from the delivery section;

a first gas pressure control means for controlling a pressure of a gas to be fed to the fine particle generating nozzle such that the particle size of the superfine particles detected by the particle size detecting means is equal to the particle size of the superfine particles set by the particle size setting means;

a secondary gas feeding means for feeding a secondary gas for increasing the fine particles in the separating vessel into the separating vessel;

a second gas pressure control means for controlling a pressure of the secondary gas to be fed by the secondary gas feeding means such that the particle size of the superfine particles detected by the particle size detecting means is equal to the particle size of the superfine particles set by the particle size setting means;

a charge supplying means for supplying charges to the superfine particles to be delivered from the delivery section; and a charge quantity control means for controlling the quantity of charges to be supplied to the superfine particles by the charge supplying means, wherein the separating vessel comprises a flow straightening member for guiding the fine particles generated by the fine particle generating nozzle to a lower part of the separating vessel, and fine particle sorting plates for restricting floating of the fine particles guided to the lower part of the separating vessel by the flow straightening member to perform sorting.

11. A suction device comprising:

a fine particle generating nozzle for generating fine particles of a substance to be sprayed by pulverizing the substance to be sprayed made of liquid by a gas;

a separating vessel for separating the fine particles generated by the fine particle generating nozzle;

a delivery section for delivering, only during suction, superfine particles separated from the fine particles in the separating vessel;

a particle size setting means for setting a particle size of the superfine particles to be delivered from the delivery section;

a particle size detecting means for detecting a particle size of the superfine particles to be delivered from the delivery section;

a first gas pressure control means for controlling a pressure of a gas to be fed to the fine particle generating nozzle such that the particle size of the superfine particles detected by the particle size detecting means is equal to the particle size of the superfine particles set by the particle size setting means;

a secondary gas feeding means for feeding a secondary gas for increasing the fine particles in the separating vessel into the separating vessel;

a second gas pressure control means for controlling a pressure of the secondary gas to be fed by the secondary gas feeding means such that the particle size of the superfine particles detected by the particle size detecting means is equal to the particle size of the superfine particles set by the particle size setting means;

a charge supplying means for supplying charges to the superfine particles to be delivered from the delivery section; and a charge quantity control means for controlling the quantity of charges to be supplied to the superfine particles by the charge supplying means, wherein the separating vessel comprises a flow straightening member for guiding the fine particles generated by the fine particle generating nozzle to a lower part of the separating vessel, and fine particle sorting plates for restricting floating of the fine particles guided to the lower part of the separating vessel by the flow straightening member to perform sorting, wherein the plurality of fine particle sorting plates respectively provided with a plurality of fine particle passing holes through which fine particles pass are disposed inside the separating vessel, and a size of the fine particle passing holes provided at the fine particle sorting plate positioned at a lower side of the separating vessel is larger than a size of the fine particle passing holes provided at the fine particle sorting plate positioned at an upper side of the separating vessel.

12. A suction device comprising:

a fine particle generating nozzle for generating fine particles of a substance to be sprayed by pulverizing the substance to be sprayed made of liquid by a gas;

a separating vessel for separating the fine particles generated by the fine particle generating nozzle;

a delivery section for delivering, only during suction, superfine particles separated from the fine particles in the separating vessel;

a recovery processing section for recovering and processing the superfine particles which have not been sucked in the delivery section;

a particle size setting means for setting a particle size of the superfine particles to be delivered from the delivery section;

a particle size detecting means for detecting a particle size of the superfine particles to be delivered from the delivery section;

a first gas pressure control means for controlling a pressure of a gas to be fed to the fine particle generating nozzle such that the particle size of the superfine particles detected by the particle size detecting means is equal to the particle size of the superfine particles set by the particle size setting means;

a secondary gas feeding means for feeding a secondary gas for increasing the fine particles in the separating vessel into the separating vessel;

a second gas pressure control means for controlling a pressure of the secondary gas to be fed by the secondary gas feeding means such that the particle size of the superfine particles detected by the particle size detecting means is equal to the particle size of the superfine particles set by the particle size setting means;

a charge supplying means for supplying charges to the superfine particles to be delivered from the delivery section; and a charge quantity control means for controlling the quantity of charges to be supplied to the superfine particles by the charge supplying means, wherein the separating vessel comprises a flow straightening member for guiding the fine particles generated by the fine particle generating nozzle to a lower part of the separating vessel, and fine particle sorting plates for restricting floating of the fine particles guided to the lower part of the separating vessel by the flow straightening member to perform sorting, wherein the plurality of fine particle sorting plates respectively provided with a plurality of fine particle passing holes through which fine particles pass are disposed inside the separating vessel, and a size of the fine particle passing holes provided at the fine particle sorting plate positioned at a lower side of the separating vessel is larger than a size of the fine particle passing holes provided at the fine particle sorting plate positioned at an upper side of the separating vessel.

13. A suction device according to any one of claims 1 to 12, further comprising:

a particle quantity setting means for setting the particle quantity of the superfine particles to be delivered from the delivery section;

a particle quantity detecting means for detecting the particle quantity of the superfine particles to be delivered from the delivery section; and a substance-to-be-sprayed quantity control means for controlling the quantity of a substance to be sprayed to be supplied to the fine particle generating nozzle such that the particle quantity of the superfine particles detected by the particle quantity detecting means is equal to the particle quantity set by the particle quantity setting means.

* * * * *